United States Patent [19]
Hanaoka et al.

[11] Patent Number: 5,284,147
[45] Date of Patent: Feb. 8, 1994

[54] ULTRASONIC PROBE TO BE INSTALLED ON FINGERTIP

[75] Inventors: Akihiko Hanaoka, Misato; Mikio Izumi, Tokyo; Yutaka Sato, Kashiwa, all of Japan

[73] Assignee: Hitachi Medical Corporation, Tokyo, Japan

[21] Appl. No.: 974,309

[22] Filed: Nov. 10, 1992

Related U.S. Application Data

[63] Continuation of Ser. No. 523,468, May 15, 1990, abandoned.

[30] Foreign Application Priority Data

May 22, 1989 [JP] Japan .................................. 1-128569

[51] Int. Cl.$^5$ .............................................. A61B 8/12
[52] U.S. Cl. .............................................. 128/662.06
[58] Field of Search ...................... 128/662.03, 662.04, 128/662.05, 662.06, 759

[56] References Cited

U.S. PATENT DOCUMENTS

| | | | |
|---|---|---|---|
| 4,545,386 | 10/1985 | Hetz et al. | 128/662.06 |
| 4,823,800 | 4/1989 | Compos | 128/661.08 |
| 4,869,260 | 9/1989 | Young et al. | 128/662.04 |
| 5,088,500 | 2/1992 | Wedel et al. | 128/662.06 |

Primary Examiner—Angela D. Sykes
Attorney, Agent, or Firm—Antonelli, Terry, Stout & Kraus

[57] ABSTRACT

The present invention relates to an ultrasonic probe to be inserted into the body of a subject for image-processing a diagnostic target thereof by ultrasonic waves transmitted to and received from the inside of the body and, more particularly, to an internal examination ultrasonic probe which can be directly installed on a palpation finger. The ultrasonic probe includes a transducer array for transmitting and receiving the ultrasonic waves; a housing for supporting the transducer array, which housing is provided with a device for installing a fingertip of an operator therein; and electric wiring members connected to the transducer array and extending from the housing to the outside so that transmission and reception signals of the ultrasonic waves are supplied therethrough. Alternatively, the ultrasonic probe includes a transducer array for transmitting and receiving the ultrasonic waves; a housing for supporting the transducer array, which housing is provided with a device for installing a fingertip of an operator therein; and electric wiring members connected to the transducer array so as to supply transmission and reception signals of the ultrasonic waves therethrough, and the electric wiring members extend from the housing to the outside in such a manner that they are located on a nail side of the fingertip or a side surface adjacent to the nail side when the fingertip is installed in the housing.

5 Claims, 2 Drawing Sheets

ULTRASONIC PROBE TO BE INSTALLED ON FINGERTIP

This application is a continuation of application Ser. No. 523,468, filed on May 15, 1990 now abandoned.

BACKGROUND OF THE INVENTION

The present invention relates to an ultrasonic probe for an ultrasonic diagnosis apparatus and, more particularly, to an improved technique which can be applied for an internal examination ultrasonic probe when it is directly installed on a palpation finger in the field of obstetrics, gynecology, urology or the like.

A conventional ultrasonic probe for an internal examination in the field of obstetrics, gynecology, urology or the like, which is inserted into the body so as to examine a diagnosis target, is of a structure that a transducer array for transmitting and receiving ultrasonic waves is located at the distal end of a rod, while a grip to be held by an operator's hand is provided at the other end of this rod. An example of such an ultrasonic probe is disclosed in the lecture article collection of the 50th congress by The Japan Society of Ultrasonic in Medicine, pp. 319-320. This transducer array has a convext shape of a small curvature diameter (about 15 mm) to effect sector scanning of the ultrasonic waves.

Palpation is often conducted in the field of obstetrics, gynecology, urology or the like. For example, in the field of obstetrics and gynecology, the internal examination has been established as a method for directly inspecting the condition of the uterus or the ovary, whereby a target organ of a subject is examined with the sense of a fingertip of a physician in such a manner that the physician's right hand is applied on the abdomen of the subject so as to hold the target organ between the right hand and the fingers of the left hand.

The conventional transvaginal ultrasonic probe includes a portion to be inserted whose distal end is 2 to 3 cm in outer diameter and a rod portion which is not less than 1 cm in diameter. Consequently, when a finger for the internal examination is accompanied with the ultrasonic probe, the overall diameter of such an insert becomes so large as to unfavorably affect the subject. Besides, since the ultrasonic probe itself is formed with the grip to be held by one hand of the physician, this hand holding the probe cannot be used for palpating the subject, hence resulting in a problem that the internal examination cannot be carried out in the above-described manner.

SUMMARY OF THE INVENTION

The present invention has been accomplished to solve the problem associated with a conventual ultrasonic probe.

One object of the present invention is to provide an ultrasonic probe with which both hands of a physician of obstetrics, gynecology, urology or the like can be employed for the palpation when the ultrasonic diagnosis is performed.

Another object of the present invention is to allow a finger with the ultrasonic probe itself to be used for the palpation by installing the ultrasonic probe on the distal end of the finger.

A still other object of the present invention is to lessen the pain of a subject to be examined by reducing the diameter of an insert when the finger and the ultrasonic probe installed thereon are inserted into the body of the subject.

A further object of the present invention is obtain a desirable ultrasonic tomogram by bringing the ultrasonic probe into contact with a diagnostic target along a direction or at an angle as the operator intends.

The other objects and some novel characteristics of the present invention invention as well as the above-described ones will be clearly understood from the descriptions in this specification with reference to the attached drawings.

BRIEF DESCRIPTION OF THE DRAWINGS

FIG. 1 is a plan of this embodiment, as viewed from an electric wiring side;

FIGS. 2 and 3 are side views of the ultrasonic probe shown in FIG. 1 in a state when the fingertip is received in it; and FIG. 4 is a side view showing an example of the fingertip ultrasonic probe in case that a transducer array of the fingertip ultrasonic probe shown in FIG. 1 is disposed at a different location.

DETAILED DESCRIPTION OF THE PREFERRED EMBODIMENTS

Figure 1:
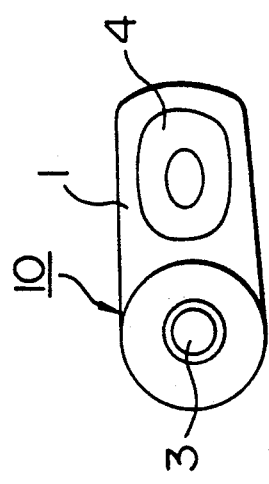
FIGS. 1 to 4 are views for schematically explaining the structure of an ultrasonic probe to be installed on a fingertip of an operator according to the first embodiment of the present invention.
Figure 2:
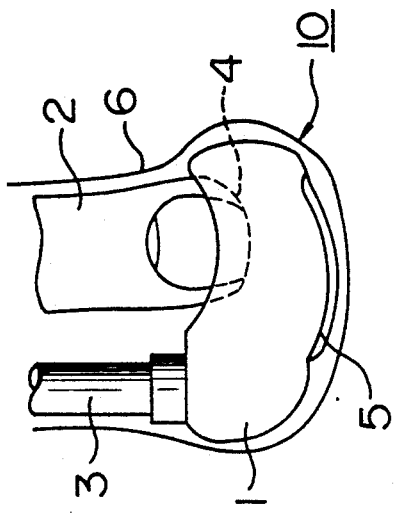
Figure 3:
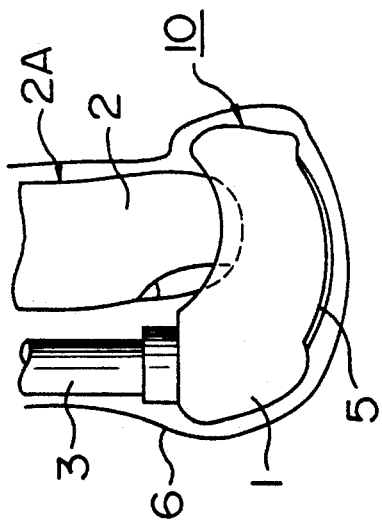
Figure 4:
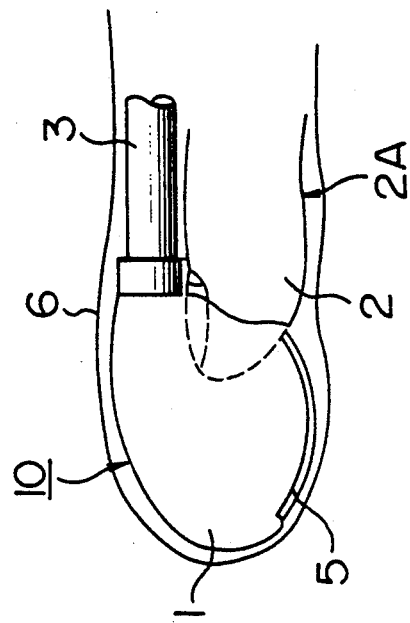

Various embodiments of the present invention will be hereinafter explained in detail with reference to the attached drawings.

In all the drawings for explaining the embodiments, members of the same function are denoted by the same reference numeral, and explanation thereof will not be therefore repeated.

Now referring to FIGS. 1 to 4, an ultrasonic probe 10 which is to be installed on the distal end of a finger according to the first embodiment is of a structure that a housing 1 is formed with a fingertip receiving recess 4 so that a portion of the housing 1 or a multicore coaxial cable (electric wiring) 3 may not be located on an inner surface side 2A of a fingertip 2 of an operator when the ultrasonic probe 10 is directly installed on the fingertip 2. In FIGS. 1 to 4, reference numeral 5 denotes an acoustic lens, i.e., a transducer array, in which a plurality of transducers are arranged in an arcuate configuration. Reference numeral 6 denotes a thin glove or fingerstall for the examination.

When the examination glove 6 is fitted on the operator's hand, the fingertip ultrasonic probe 10 of the first embodiment is set at a location within the examination glove 6 corresponding to the fingertip 2, as shown in the drawings. In this case, the recess 4 formed in the housing 1 and the examination glove 6 serve to secure the ultrasonic probe 10 against the fingertip 2.

It is clearly understood from the above explanation with respect to the first embodiment that the housing 1 is provided with the fingertip receiving recess 4 formed therein in such a manner that the multicore coaxial cable (electric wiring) 3 of the housing 1 may not be located on the inner surface side 2A of the fingertip 2 of the operator while the ultrasonic probe 10 being directly attached on the fingertip 2. As a result, when the ultrasonic probe 10 is installed on the fingertip 2 of the operator in actual use, the multicore coaxial cable (electric wiring) 3 of the housing 1 does not occupy a position on the inner surface side 2A of the finger tip 2, and consequently, when the fingertip 2 on which the ultrasonic probe 10 is attached in this manner is inserted into a body cavity of a subject to be examined (patient), the inside of the body cavity can be desirably palpated by means of the inner surface side 2A of the fingertip 2 with the ultrasonic probe 10.

Thus, the inside of the body cavity of the subject can be examined by means of the sense of the fingertip so that the ultrasonic diagnosis can be performed while palpating the subject with both hands. In obstetrics and gynecology, for example, as a method for directly inspecting the condition of the uterus or the ovary, it is possible to examine a target organ with the sense of the fingertip in such a manner that the right hand of the operator is applied on the abdomen of the subject so as to hold the target organ between the right hand and the fingers of the left hand.

Further, since the ultrasonic probe 10 can be easily installed on the fingertip 2 of the operator by fitting the fingertip 2 into the fingertip receiving recess 4 of the housing 1 of the ultrasonic probe 10, the fingertip 2 of the operator and the ultrasonic probe 10 can be integrally connected with each other, thereby enabling the ultrasonic diagnosis by palpating the subject with both hands of the operator. Also, the finger with the probe itself can be used for the palpation. Moreover, the integral connection of the fingertip 2 of the operator and the ultrasonic probe 10 will improve the efficiency in operation of the ultrasonic probe 10 so that an ultrasonic tomogram at an arbitrary angle can be supplied as the operator intends, and therefore, it is possible to perform the ultrasonic diagnosis with accuracy.

Figure 5:
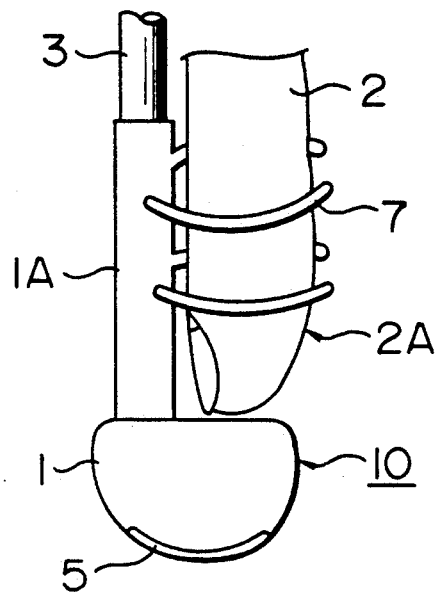
FIG. 5 is a view for schematically explaining the structure of a fingertip ultrasonic probe according to the second embodiment of the present invention.

A fingertip ultrasonic probe of the second embodiment is shown in FIG. 5. This ultrasonic probe is of a structure that a column 1A of the housing 1 is provided with fingertip receiving ring-like members 7 in place of the fingertip receiving recess 4 of the first embodiment described above, so that the multicore coaxial cable (electric wiring) 3 may not be located on the inner surface side 2A of the fingertip 2 of the operator when the ultrasonic probe 10 is directly installed on the fingertip 2. It should be noted that each ring-like member 7 preferably has a cut-off portion at the intermediate area to allow the inner surface of the fingertip to be employed for the palpation.

According to the structure described above, the ultrasonic probe of the second embodiment can take the same advantageous effect as that of the first embodiment.

Figure 6:
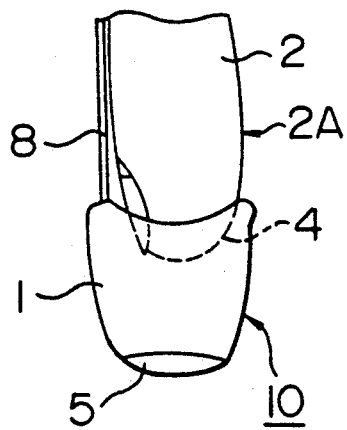
FIGS. 6 and 7 are views for schematically explaining the structure of a fingertip ultrasonic probe according to the third embodiment of the present invention.
Figure 7:
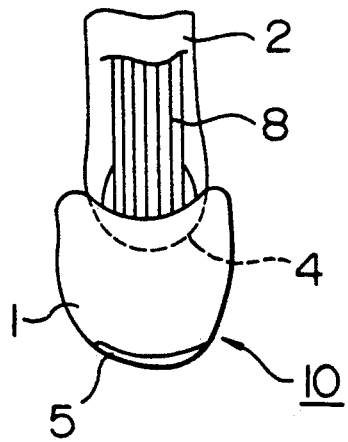

A fingertip ultrasonic probe of the third embodiment is shown in FIGS. 6 and 7. Instead of the multicore coaxial cable 3 of the first embodiment described above, this ultrasonic probe is provided with flexible wiring means such as a flexible substrate or a flat cable 8 which comprises a plurality of conductive elements in a single layer or a plurality of layers disposed in parallel and extending on a plane.

According to this structure, since the fingertip ultrasonic probe 10 can be easily installed on the fingertip 2 of the operator, the fingertip 2 and the ultrasonic probe 10 can be integrally connected with each other, thereby enabling the ultrasonic diagnosis by palpating the subject with both hands. Moreover, the integral connection of the fingertip 2 of the operator and the ultrasonic probe 10 will improve the efficiency in operation of the ultrasonic probe 10 so that an ultrasonic tomogram at an arbitrary angle can be supplied as the operator intends, and therefore, it is possible to perform the ultrasonic diagnosis with accuracy. Furthermore, the electric wiring is closely accompanied with the finger, and consequently, the overall diameter of the wiring and the finger can be made smaller so as to lessen the subject's pain when the finger and the probe installed thereon are inserted into the body of the subject.

Needless to say, although the present invention has been concretely described heretofore on the basis of the preferred embodiments, the invention is not restricted within these embodiments, and various modifications may be made without departing from the true spirit and scope of the invention.

What is claimed is:

1. An ultrasonic probe to be inserted into a body of a subject for image-processing a diagnostic target of the subject by means of ultrasonic waves transmitted to and received from an inside of the body comprising:
   a transducer array for transmitting and receiving the ultrasonic waves;
   a housing coupled to said transducer array, said housing being provided with a recess, having a depth corresponding to a length from a tip of a finger of an operator to at most a point within a nail of the finger, for receiving the tip of the finger of the operator, said housing being constructed to permit a portion of the side of the finger directly opposite the nail and said transducer array to both be in contact with the same surface area of the diagnostic target; and
   electric wiring means connected to said transducer array and extending from said housing to the outside so that transmission and reception signals of the ultrasonic waves are supplied therethrough.

2. An ultrasonic probe according to claim 1 wherein said recess is formed on one of a back side and a lateral side with respect to a surface of said housing where said transducer array is provided.

3. An ultrasonic probe according to claim 1 wherein said electric wiring means is located in a direction substantially parallel with a direction of the depth of the recess.

4. An ultrasonic probe according to claim 3, wherein said electric wiring means is either a flexible substrate or a flat cable.

5. An ultrasonic probe to be inserted into a body of a subject for image-processing a diagnostic target of the subject by means of ultrasonic waves transmitted to and received from an inside of the body, comprising:
   a transducer array for transmitting and receiving the ultrasonic waves;
   a housing coupled to said transducer array;
   an annular member secured in said housing for allowing a finger of the operator to be inserted therein, an annular configuration of said member being broken at on portion to permit a side of the finger of the operator opposite the nail of the finger to contact the surface of the body; and
   electric wiring means connected to said transducer array and extending from said housing to the outside so that transmission and reception signals of the ultrasonic waves are supplied therethrough.

* * * * *